(12) United States Patent
Dai et al.

(10) Patent No.: US 9,827,080 B2
(45) Date of Patent: Nov. 28, 2017

(54) HEAD STRUCTURE OF A BRUSH APPLIANCE

(71) Applicant: SHANGHAI SHIFT ELECTRICS CO., LTD, Shanghai (CN)

(72) Inventors: Xiaoguo Dai, Shanghai (CN); Zhenwu Xu, Shanghai (CN)

(73) Assignee: SHANGHAI SHIFT ELECTRICS CO., LTD., Shanghai (CN)

( * ) Notice: Subject to any disclaimer, the term of this patent is extended or adjusted under 35 U.S.C. 154(b) by 355 days.

(21) Appl. No.: 14/417,123

(22) PCT Filed: Apr. 3, 2013

(86) PCT No.: PCT/CN2013/073728
§ 371 (c)(1),
(2) Date: Jan. 23, 2015

(87) PCT Pub. No.: WO2014/015683
PCT Pub. Date: Jan. 30, 2014

(65) Prior Publication Data
US 2015/0202031 A1    Jul. 23, 2015

(30) Foreign Application Priority Data
Jul. 23, 2012    (CN) .......................... 2012 1 0254085

(51) Int. Cl.
*A61C 17/34*       (2006.01)
*A61C 17/22*       (2006.01)
*A46B 13/02*       (2006.01)

(52) U.S. Cl.
CPC ........ *A61C 17/349* (2013.01); *A61C 17/3418* (2013.01); *A61C 17/3472* (2013.01); *A46B 13/02* (2013.01); *A61C 17/3436* (2013.01)

(58) Field of Classification Search
CPC ......... A61C 17/22; A61C 17/32; A61C 17/34; A61C 17/3409; A61C 17/3418;
(Continued)

(56) References Cited

U.S. PATENT DOCUMENTS 5,046,213 A    9/1991 Curtis et al.
5,259,083 A    11/1993 Stansbury, Jr.
(Continued)

FOREIGN PATENT DOCUMENTS

CN    1055472 A    10/1991
CN    2892005 Y    4/2007
(Continued)

OTHER PUBLICATIONS

International Search Report dated Jul. 18, 2013 (PCT/CN2013/073728); ISA/CN.
(Continued)

*Primary Examiner* — Mark Spisich
(74) *Attorney, Agent, or Firm* — Banner & Witcoff, Ltd.

(57) ABSTRACT

A head structure of a brush appliance comprises a frame movably connected with a head driving shaft, driving bristle retainers connected with and driven by the head driving shaft, and driven bristle retainers which and the driving bristle retainers are alternatively arranged with each other. In the head structure, the driven bristle retainers are driven by the driving bristle retainers from the frame in a constrained mode and move around a respective motion axis. The driving bristle retainers have protrusions. The driven bristle retainers have bevel surfaces which correspondingly cooperate with the protrusions. At least one driven point on at least one of bevel surfaces is closer to the driving bristle retainers than a contact point or a contact line or a contact surface of the at least bevel surface and the corresponding
(Continued)

protrusions. Thereby the driven bristle retainers are driven by the driving bristle retainers in the moving process.

20 Claims, 10 Drawing Sheets

(58) Field of Classification Search
CPC ... A61C 17/3472; A61C 17/349; A61C 17/40; A46B 13/02; A46B 13/023
USPC ........................................ 15/22.1, 22.2, 22.4
See application file for complete search history.

(56) References Cited

U.S. PATENT DOCUMENTS

| | | | |
|---|---|---|---|
| 5,504,958 A | | 4/1996 | Herzog |
| 6,553,604 B1 | | 4/2003 | Braun et al. |
| RE44,819 E | | 4/2014 | Braun et al. |
| 2003/0084525 A1* | 5/2003 | Blaustein ............ A61C 17/3472 15/22.1 |
| 2003/0140435 A1* | 7/2003 | Eliav ................... A61C 17/349 15/22.1 |
| 2009/0049626 A1 | | 2/2009 | Eliav et al. |
| 2010/0036656 A1 | | 2/2010 | Kawashima et al. |

FOREIGN PATENT DOCUMENTS

| | | | |
|---|---|---|---|
| CN | 101194784 A | | 6/2008 |
| CN | 102743016 A | | 10/2012 |
| CN | 202932303 U | | 5/2013 |
| DE | 29513429 | * | 10/1995 |
| DE | 29600236 | * | 3/1996 |
| DE | 29613608 | * | 10/1996 |
| DE | 202008005856 U1 | | 9/2008 |
| EP | 0449653 A1 | | 10/1991 |
| GB | 2237505 | * | 5/1991 |
| GB | 2247296 | * | 2/1992 |
| JP | 2-218309 | * | 8/1990 |
| WO | 0238004 A1 | | 5/2002 |
| WO | 2011073912 A2 | | 6/2011 |

OTHER PUBLICATIONS

Jan. 27, 2015—(WO) International Preliminary Report on Patentability—PCT/CN2013/073728.

Nov. 15, 2013—(CN) First Office Action—App 201210254085.7.

* cited by examiner

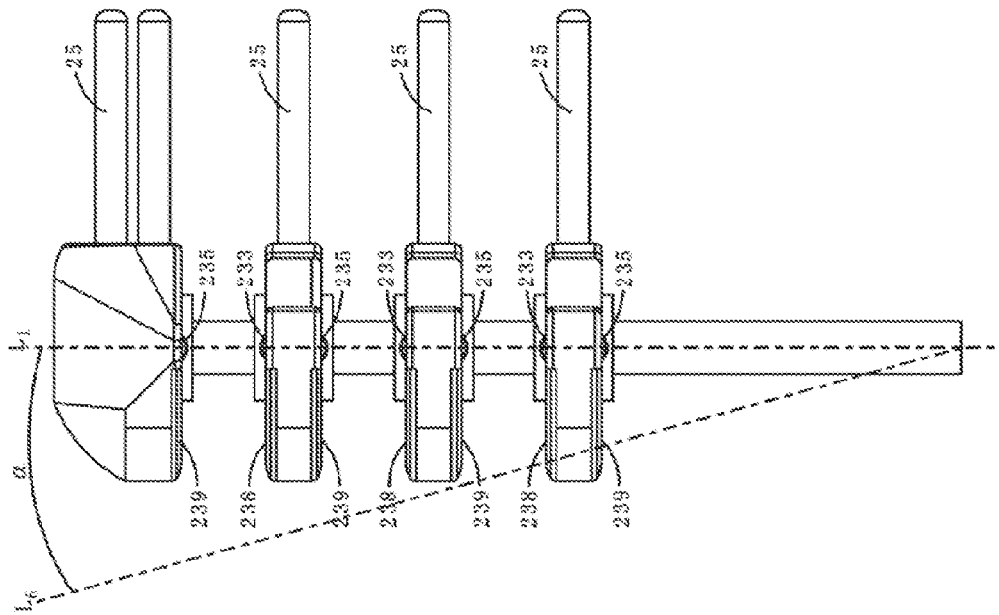
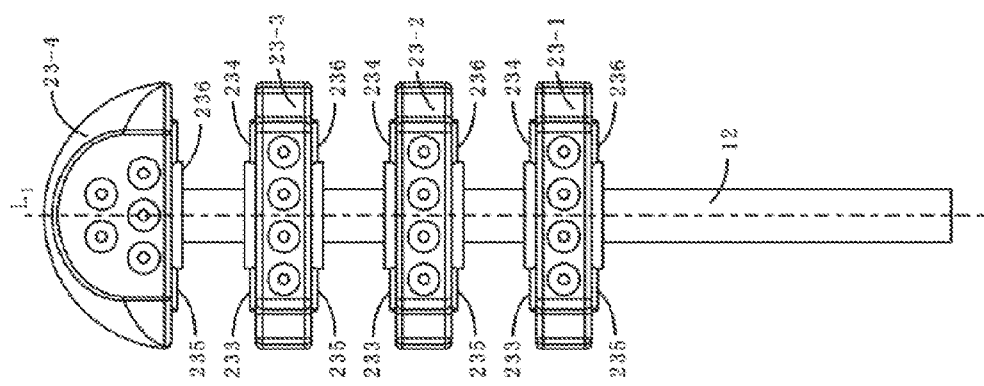
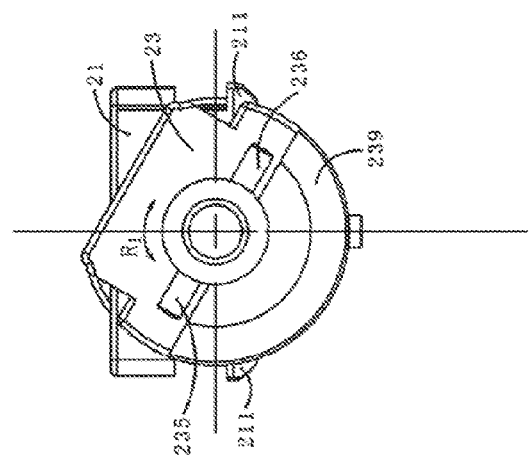
Fig. 7
Fig. 6
Fig. 5

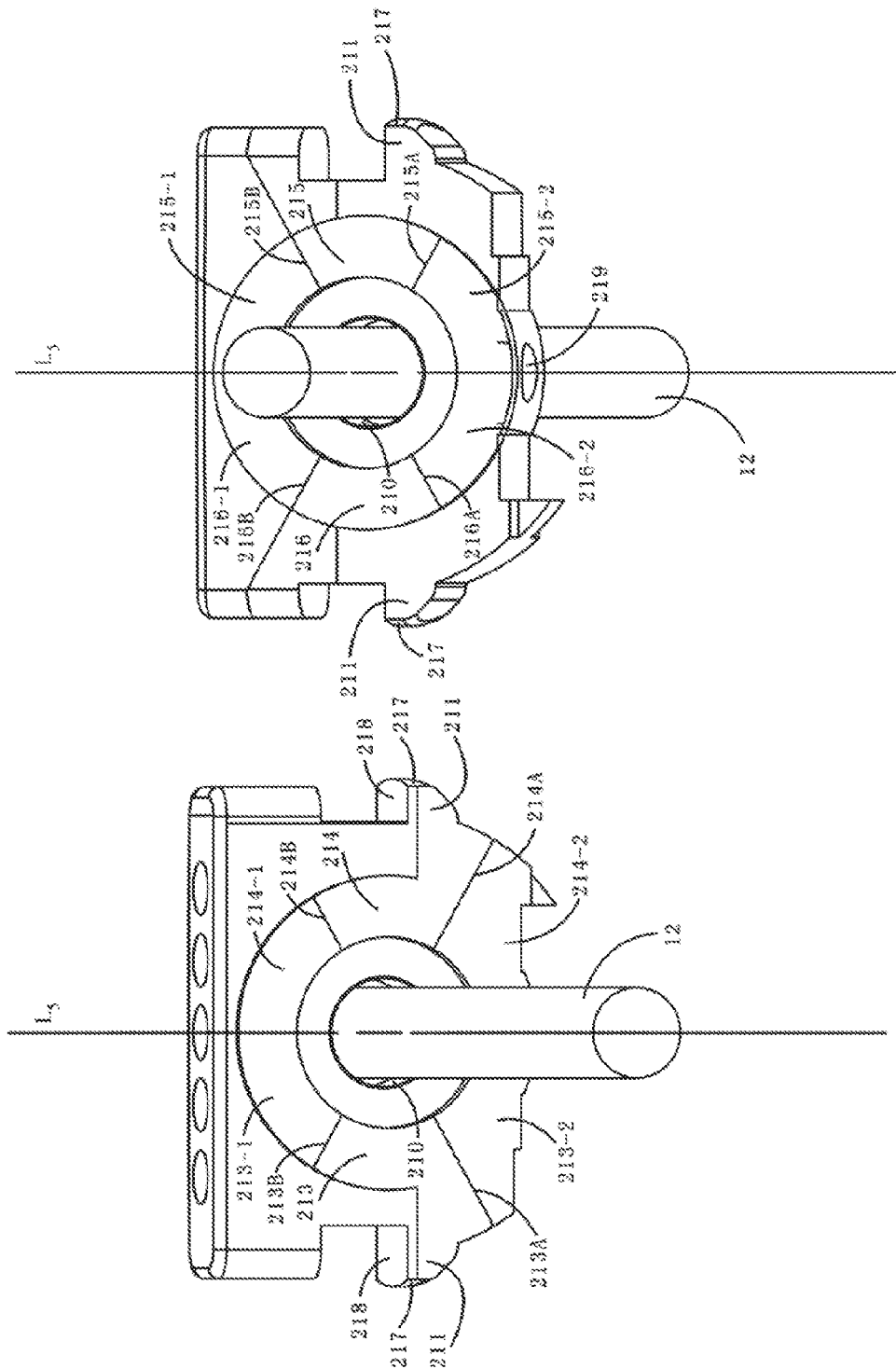

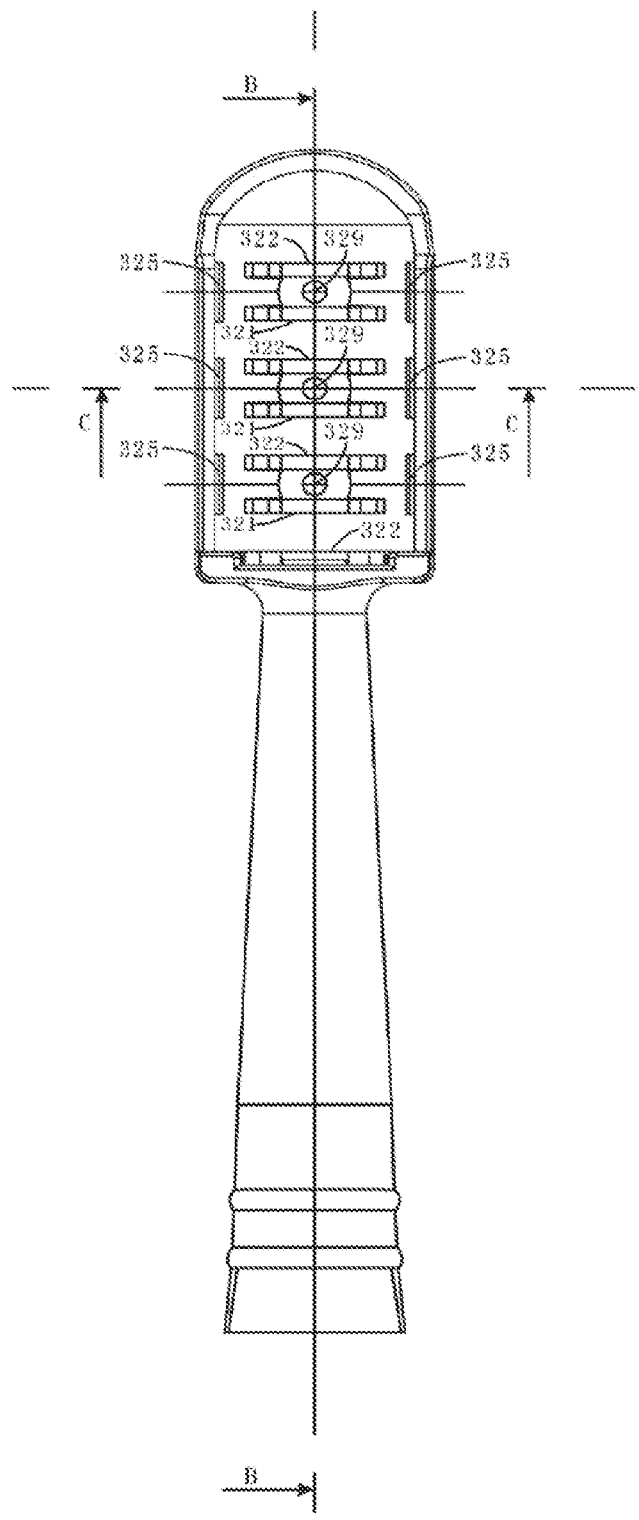
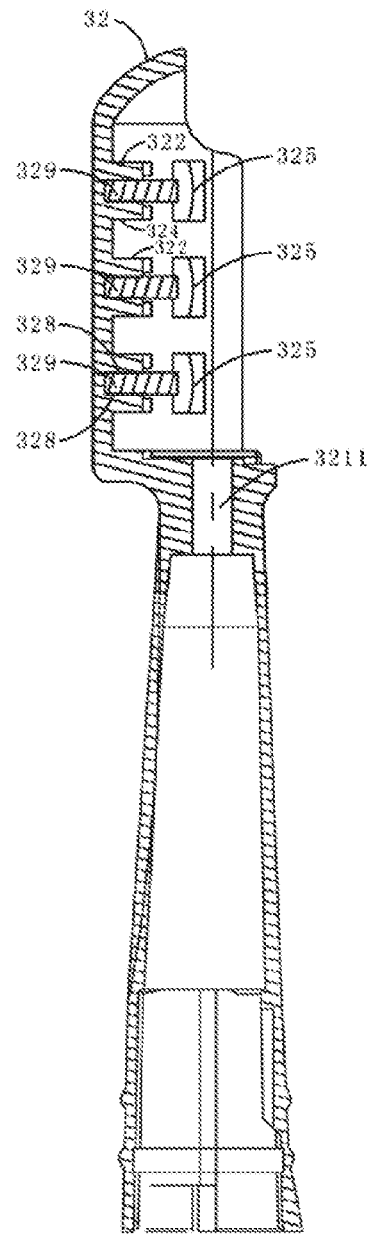
Fig. 15
Fig. 16

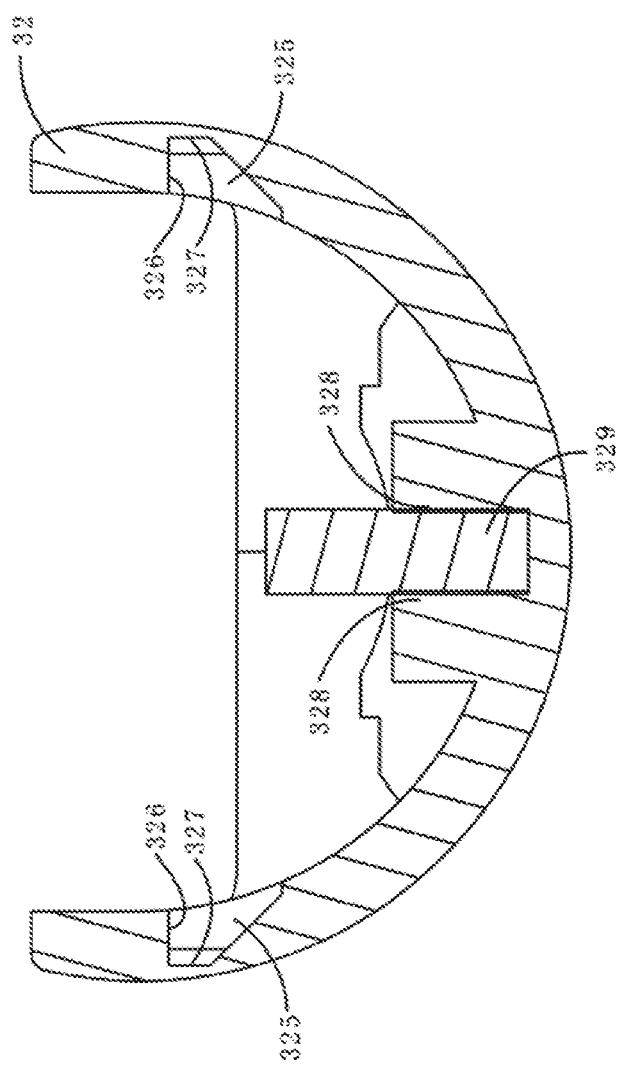

HEAD STRUCTURE OF A BRUSH APPLIANCE

CROSS-REFERENCE TO RELATED APPLICATION

This application is the National Stage of International Application No. PCT/CN2013/073728, filed on Apr. 3, 2013, and claiming priority to Chinese Patent Application No. CN201210254085.7 filed on Jul. 23, 2012, which is incorporated herein by reference.

FIELD OF THE INVENTION

The present invention relates to a head structure of a brush appliance, in particular to a head structure of a brush appliance such as a toothbrush.

BACKGROUND OF THE INVENTION

The head structure of a brush appliance is of crucial importance for the cleaning effect and other extended functions of the brush. Therefore, a variety of improvements have been made to the head structure of brush appliance.

US2010/0036656A1 discloses a brush part of an electric toothbrush, which has a head and comprises a frame, a movable contact element retainer, and an extension part of the movable contact element retainer. The frame comprises a plurality of first contact elements supported in it. The movable contact element retainer comprises a plurality of second contact elements supported in it, and is configured to receive the energy for cleaning movement from an electric driver, such that it has at least one free movement in relation to the first contact elements. The extension part of the movable contact element retainer is arranged on the top of the head, with clearance between the extension part and the frame, wherein, the width of at least a first part of the clearance in the side edge area of the head part is smaller than the width of a second part of the clearance in the inner area of the head.

SUMMARY OF THE INVENTION

The object of the present invention is to provide a head structure of a brush appliance, in particular a head structure of a brush appliance such as a toothbrush, which not only has excellent cleaning effect but also has other secondary functions, such as massaging.

To attain the object described above, according to an aspect of the present invention, the present invention provides a head structure of a brush appliance, comprising: a frame movably connected with a head driving shaft; a plurality of driving bristle retainers connected with the head driving shaft and driven by the head driving shaft, designed to receive bristles mounted on them; and one or more driven bristle retainers, which and the driving bristle retainers are alternatively arranged with each other, and designed to receive bristles mounted on it/them, wherein, the one or more driven bristle retainers is/are driven by the driving bristle retainers under the constraint of the frame to move around their respective movement axes; at least one of the plurality of driving bristles retainers has at least one protrusion on a surface perpendicular to an axis of the head driving shaft, and the one or more driven bristle retainers has/have at least one bevel face that cooperates with the protrusions on its/their surfaces where the one or more driven bristle retainers is/are driven by the driving bristle retainers; and at least one contact line on the at least one bevel face is closer to the driving bristle retainer than other contact lines of the bevel face with the corresponding protrusion, such that the driven bristle retainer is driven by the driving bristle retainer in the movement process.

Preferably, the head driving shaft moves as a motor-driven holder driving shaft of the brush appliance moves.

Moreover, the driving bristle retainer may have at least two protrusions that attain effects opposite to each other during operation, and the driven bristle retainer has bevel faces that cooperate with the protrusions on the end face where the driven bristle retainer is driven by the driving bristle retainer. The first protrusion is arranged on an upper end face of the driving bristle retainer in upward direction parallel to the axis of the head driving shaft, and the second protrusion is arranged on a lower end face of the driving bristle retainer opposite to the upper end face, and the first protrusion and second protrusion can be on the same side in relation to the axis of the head driving shaft.

In another embodiment, the driving bristle retainer has a first and a second protrusions that attain effects opposite to each other during operation, and the driven bristle retainer has bevel faces that cooperate with the first and second protrusions on a surface where the driven bristle retainer is driven by the driving bristle retainer. Both the first protrusion and the second protrusion are arranged on an upper surface of the driving bristle retainer along the axis of the head driving shaft, or both of them are arranged on a lower surface of the driving bristle retainer along the axis of the head driving shaft. In addition, the first protrusion and the second protrusion are arranged on the upper surface or lower surface on different sides in relation to the axis of the head driving shaft.

Optionally, the driving bristle retainer may have a first and a second groups of protrusions. A first group of protrusions and a second group of protrusions are opposite to each other in protruding direction. The first group of protrusions is arranged on an upper surface of the driving bristle retainer along the axis of the head driving shaft and laterally symmetric in relation to the axis of the head driving shaft, the second group of protrusions is arranged on a lower surface of the driving bristle retainer along the axis of the head driving shaft and laterally symmetric in relation to the axis of the head driving shaft, and the protrusions that are opposite to each other in protruding direction on the same side in relation to the axis of the head driving shaft are symmetric in relation to a plane that contains the center line of the driving bristle retainer in the thickness direction and is perpendicular to the axis of the head driving shaft.

According to another aspect of the present invention, the present invention provides a head structure of a brush appliance, comprising: a frame movably connected with a head driving shaft; a plurality of driving bristle retainers connected with the head driving shaft and driven by the head driving shaft, designed to receive bristles mounted on them; and one or more driven bristle retainers, which and the driving bristle retainers are alternatively arranged with each other, and designed to receive bristles mounted on it/them, wherein, the driven bristle retainers are driven by the driving bristle retainers under the constraint of the frame to move around their respective movement axes; at least one of the plurality of driving bristle retainers has at least one bevel face on a surface along the axis of the head driving shaft, and the one or more driven bristle retainer has/have at least one protrusion that cooperates with the at least one bevel face on its/their surfaces where the one or more driven bristle retainers is/are driven by the driving bristle retainer; and at least one driven line on the at least one bevel face is closer to the driven bristle retainer than other contact lines of the bevel face with the corresponding protrusion, such that the one or more driven bristle retainer is/are driven by the driving bristle retainers in the movement process.

In that case, other additional technical features are similar to those in the above-mentioned technical scheme in which the driving bristle retainer has protrusions on a surface and the driven bristle retainer has bevel faces that cooperate with the protrusions on an corresponding end face, with the only difference lying in: the driving bristle retainer has bevel faces on a surface, while the driven bristle retainer has protrusions that cooperate with the bevel faces on an corresponding surface. Preferably, the movement axis of the driven bristle retainer is perpendicular to the axis of the head driving shaft, the driving bristle retainer can swing around the axis of the head driving shaft, and the driven bristle retainers can swing around their respective movement axes.

The driving bristle retainer can revolve by angle γ around the axis of the head driving shaft, and accordingly, the driven bristle retainers can revolve by angle σ around their respective movement axes. The angle γ is 30°~70°, and the angle σ is 1°~8°. Preferably, the angle γ is 60°, and the angle σ is 4°.

The head structure provided in the present invention is simple and compact, and not only attains excellent cleaning effect but also provides other secondary functions, such as massaging.

DESCRIPTION OF THE DRAWINGS

FIG. 5 is a bottom view illustrating the relative movement of the driving bristle retainer and driven bristle retainer in FIG. 4.

FIG. 6 is a front view, with the driven bristle retainers shown in FIG. 2 removed.

FIG. 7 is a left view corresponding to FIG. 6.

FIG. 13 is a perspective view illustrating the assembling relation between the driven bristle retainer and the head driving shaft.

FIG. 14 is a rear view corresponding to FIG. 13.

FIG. 15 is a front view, showing the assembling relation between the brush holder and the driven bristle retainer movement shaft.

FIG. 16 is a sectional view of the structure shown in FIG. 15 in direction B-B.

FIG. 17 is a sectional view of the structure shown in FIG. 15 in direction C-C.

Figure 1:
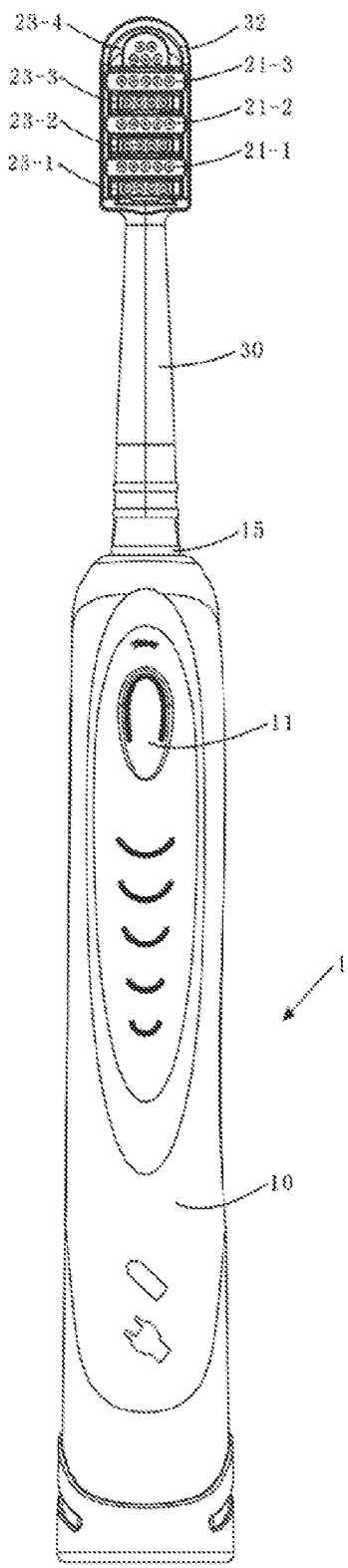
FIG. 1 is a front view of an electric toothbrush.
Figure 2:
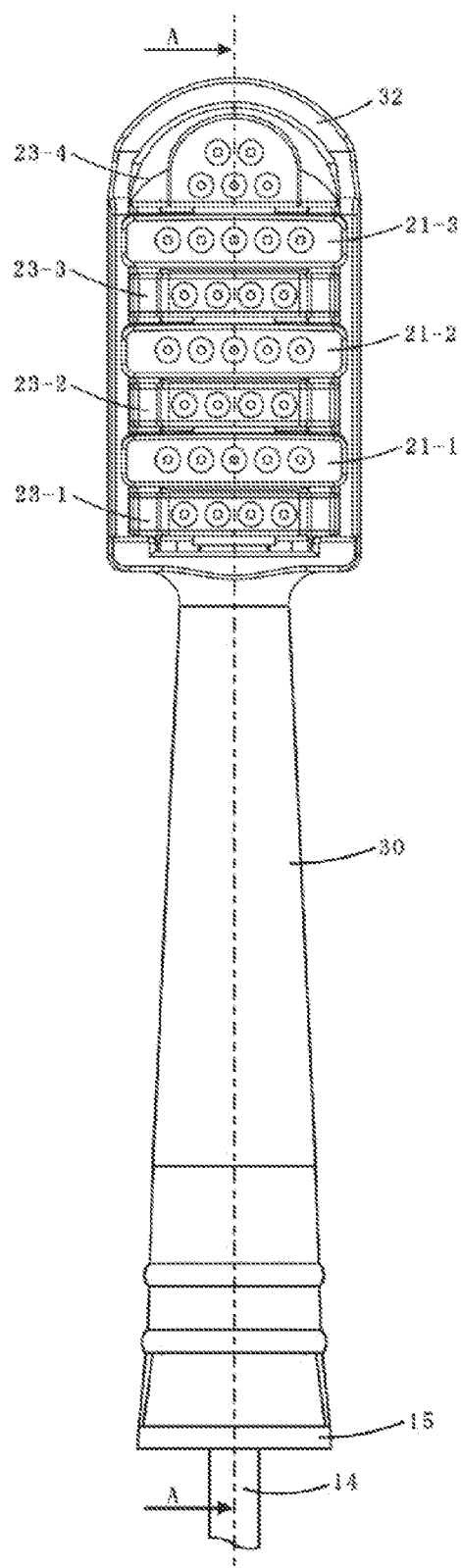
FIG. 2 is a front view of the brush part, showing a head that comprises a plurality of driving bristle retainers and a plurality of driven bristle retainers.

BRIEF DESCRIPTION OF THE SYMBOLS $L_0$: axis of the holder driving shaft;
$L_1$: axis of the head driving shaft;
$L_4$, $L_3$, and $L_2$: movement axes of the first, the second, and the third driven bristle retainers respectively;
$L_5$: revolving angle β around $L_1$;
$L_6$: revolving angle α around $L_1$;
$R_0$: moving direction of the holder driving shaft;
$R_1$: moving direction of the head driving shaft;
$R_4$, $R_3$, and $R_2$: moving directions of the first, the second, and the third driven bristle retainers respectively;
1: electric toothbrush;
10: holder;
11: switch;
12: head driving shaft;
14: holder driving shaft connected with a driving motor;
15: interface;
16: connector;
30: brush part;
32: frame;
23-1, 23-2, 23-3, and 23-4: first, second, third, and fourth driving bristle retainers;
21-1, 21-2, and 21-3: first, second, and third driven bristle retainers;
25: bristles fixed to the driving bristle retainer;
27: bristles fixed to the driven bristle retainer;
233, 234, 235, and 236: protrusions arranged on the upper end face and lower end face of the driving bristle retainer;
213, 214, 215, and 216: bevel faces arranged on the upper end face and lower end face of the driven bristle retainer, corresponding to the movement traces of the protrusions 233, 234, 235, and 236 on the driving bristle retainer;
210: mating face between the driven bristle retainer and the head driving shaft;
211: snap parts on both sides of the driven bristle retainer;
219: movement hole of the driven bristle retainer;
217: side arc surfaces of the snap part of the driven bristle retainer;
218: upper flat surface of the snap part of the driven bristle retainer;
238: arc surface on the edge of the lower part of the driving bristle retainer in $W_2$ direction;
239: arc surface on the edge of the lower part of the driving bristle retainer in $W_1$ direction;
321: facet on the cavity bottom of the frame, which contacts with the arc surface on the edge of the lower part of the driving bristle retainer in $W_2$ direction;
322: facet on the cavity bottom of the frame, which contacts with the arc surface on the edge of the lower part of the driving bristle retainer in $W_1$ direction;
325: slots on the frame, designed to accommodate the snap parts on both sides of the driven bristle retainer;
326: flat surface of the slot in $W_4$ direction, corresponding to the upper flat surface of the snap part of the driven bristle retainer;
327: inner curved surface of the slot;

328: movement center hole of the driven bristle retainer on the frame;

329: driven bristle retainer movement shaft

DETAILED DESCRIPTION OF THE EMBODIMENTS

Hereunder some exemplary embodiments of the present invention will be further detailed in the case of an electric toothbrush, with reference to the accompanying drawings. Though the present invention will be described hereunder in the case of an electric toothbrush, the present invention is not limited to that. Apparently, the present invention is also applicable to non-electric toothbrushes or other brushes.

Among the accompanying drawings, similar parts are identified by similar symbols.

For the purpose of clarity, in this specification, terms that represent relative spatial positions such as "up", "down", "upper part", "lower part", "left", and "right" are used to describe the positional relationship between one element or feature and another one or more elements or one or more features. "Up", "down", "upper part", and "lower part" are described in relation to the axis of the head driving shaft, the upward direction parallel to the axis of the head driving shaft in a view is defined as "up" or "upper part", while the downward direction parallel to the axis of the head driving shaft in a view is defined as "down" or "lower part". "Left" and "right" are described in relation to the axis of the head driving shaft, the direction perpendicular to the axis of the head driving shaft and on the left of the axis of the head driving shaft is defined as "left", and accordingly, the direction perpendicular to the axis of the head driving shaft and on the right of the axis of the head driving shaft is defined as "right".

Though terms "first" and "second" and the like are used to describe a plurality of elements or constituents in this specification, these elements or constituents are not subject to the limitation of those terms. Those terms are only used to differentiate one element or constituent from another, instead of constituting any "order". Therefore, any exchange of the ordinals of those elements or constituents to be discussed below is not beyond the concept and scope of the present invention.

In addition, the term "and/or" used in this patent application covers any combination or all combinations of the listed one or more associated words or phrases.

Figure 11:
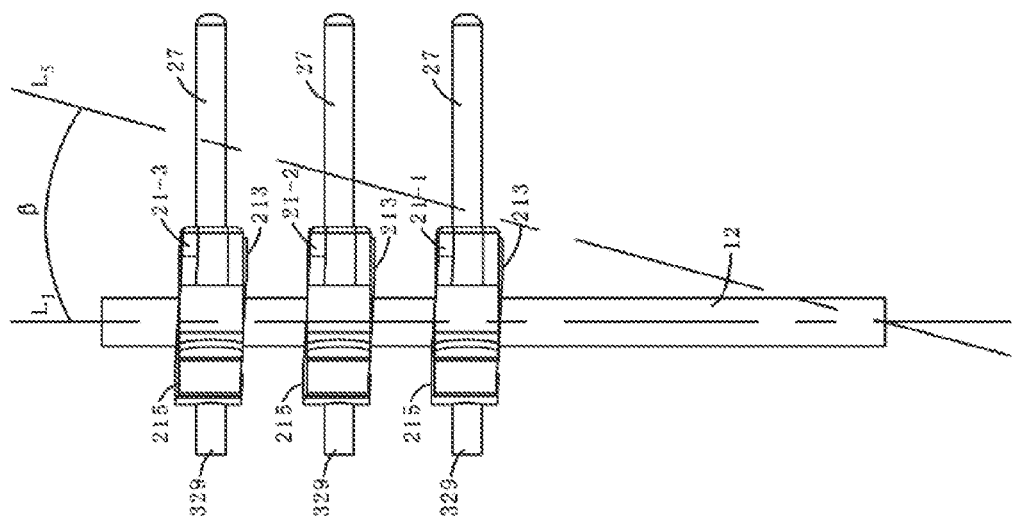
FIG. 11 is a left view corresponding to FIG. 10.

Please see FIGS. 1-5, in an embodiment of the present invention, an electric toothbrush 1 comprises a removable brush part 30 and a holder part 10. The removable brush part 30 comprises: a head, a head driving shaft 12, a connector 16, and an interface 15. The head comprises: a frame 32 movably connected with the head driving shaft 12; driving bristle retainers 23-1, 23-2, 23-3, and 23-4; driven bristle retainers 21-1, 21-2, and 21-3; bristles 25 mounted on the driving bristle retainers 23-1, 23-2, 23-3, and 23-4 respectively and bristles 27 mounted on the driven bristle retainer 21-1, 21-2, and 21-3 respectively; and, driven bristle retainer movement shafts 329 (see FIG. 5 and FIG. 11). The driving bristle retainers 23-1, 23-2, 23-3, and 23-4 and the driven bristle retainers 21-1, 21-2, and 21-3 are arranged alternatively. The driven bristle retainers 21-1, 21-2, and 21-3 can receive kinetic energy from the driving bristle retainers 23-1, 23-2, 23-3, and 23-4, and move accordingly. The driven bristle retainer movement shafts 329 are in the same quantity as the driven bristle retainers 21-1, 21-2, and 21-3. The driving bristle retainers 23-1, 23-2, 23-3, and 23-4 and the driven bristle retainers 21-1, 21-2, and 21-3 match in shape, and they can be in any shape. For the convenience of use, the thickness is by far smaller than the width, and the width is smaller than the length. The connector 16 is designed to connect the head driving shaft 12 with the holder driving shaft 14. The head driving shaft 12 swings as the holder driving shaft 14 revolves or swings. The interface 15 is designed to assemble up the brush part 30 and the holder part 10.

As shown in the figures, though the driving bristle retainers are in a quantity of four (i.e., 23-1, 23-2, 23-3, and 23-4) and the driven bristle retainer are in a quantity of three (i.e., 21-1, 21-2, and 21-3) in this embodiment, the driving bristle retainers and driven bristle retainers can be configured as required in terms of the quantity, and they may be in the same quantity or in different quantities (as in the case of this embodiment).

When the user presses a switch 11 (FIG. 1) on the holder 10 of the electric toothbrush, an electric motor (not shown) in the holder 10 of the electric toothbrush 1 will be started to drive the holder driving shaft 14 to move around its axis $L_0$ (for example, in this embodiment, the holder driving shaft 14 swings around the axis $L_0$; of course, the holder driving shaft 14 may revolve around the axis $L_0$, alternatively) via an ordinary transmission mechanism, and the holder driving shaft 14 transfers the kinetic energy via the connector 16 to the head driving shaft 12, such that the head driving shaft 12 moves around its axis $L_1$. As an example, in this embodiment, the head driving shaft 12 swings around its axis $L_1$. The head driving shaft 12 runs through all driven bristle retainers 21-1, 21-2, and 21-3 on the head with clearance and are connected with all driving bristle retainers 23-1, 23-2, 23-3, and 23-4 without relative movement; in addition, the head driving shaft 12 is connected with the connector 16 without relative movement. The driving bristle retainers 23-1, 23-2, 23-3, and 23-4 swing as the head driving shaft 12 swings around its axis $L_1$, and the driving bristle retainers 23-1, 23-2, 23-3, and 23-4 can drive the driven bristle retainers 21-1, 21-2, and 21-3 to swing around their respective movement axes $L_4$, $L_3$, and $L_2$ via the transmission mechanism arranged between the driving bristle retainers 23-1, 23-2, 23-3, and 23-4 and the driven bristle retainers 21-1, 21-2, and 21-3. In this embodiment, the driven bristle retainers 21-1, 21-2, and 21-3 swing around their respective movement axes $L_4$, $L_3$, and $L_2$ perpendicular to the axis $L_1$ of the head driving shaft 12, such that the bristles 25 fixed on the driving bristle retainers 23-1, 23-2, 23-3, and 23-4 essentially swing around the axis $L_1$ of the head driving shaft 12 and the bristles 27 fixed on the driven bristle retainers 21-1, 21-2, and 21-3 essentially swing around their respective movement axes $L_4$, $L_3$, and $L_2$.

There is no restriction on the transmission mechanism for the holder 10 in the present invention, which is to say, the transmission mechanism can be any known mechanism that can transfer the kinetic energy of the electric motor to the holder driving shaft 14 to drive the holder driving shaft 14 to move (revolve or swing). Likewise, there is no restriction on the transmission mechanism for the head driving shaft 12 in the present invention, which is to say, the transmission mechanism can be any known mechanism that can transfer the kinetic energy of the holder driving shaft 14 to the head driving shaft 12 to drive the head driving shaft 12 to move (revolve or swing). In this embodiment, the transmission mechanism is a known transmission mechanism that can cause the holder driving shaft 14 and head driving shaft 12 to swing respectively.

In another embodiment, the head driving shaft 12 can be arranged in parallel to the head driving shaft and off-center the axis of the fixed shaft, and can swing around the axis of the fixed shaft. The driving bristle retainer has a hole that is fitted to the fixed shaft and in diameter greater than the diameter of the fixed shaft; thus, the driving bristle retainer is connected with the fixed shaft in a way that it can move in relation to the fixed shaft. The driving bristle retainer is driven by the head driving shaft 12 to swing around the axis of the fixed shaft. The driving bristle retainer has a hole that is fitted to the head driving shaft 12 and in diameter greater than the diameter of the head driving shaft 12; thus, the driving bristle retainer is connected with the head driving shaft 12 in a way that it can move in relation to the head driving shaft 12.

As shown in FIGS. 2-5, in this embodiment, the driving bristle retainers 23-1, 23-2, 23-3, and 23-4 can be arranged in a top-to-bottom order in the $W_1$ direction of the axis $L_0$ of the holder driving shaft 14, for example, the fourth driving bristle retainer 23-4 can be arranged on the top, the third and the second driving bristle retainers 23-3 and 23-2 can be arranged in succession below the fourth driving bristle retainer 23-4, and the first driven bristle retainer 23-1 can be arranged on the bottom. The bristles 25 can be fixed to the four driving bristle retainers 23-1, 23-2, 23-3, and 23-4 respectively through any industrial brush manufacturing process.

Each of the driving bristle retainers 23-1, 23-2, 23-3, and 23-4 has a hole that can be arranged around the axis $L_1$ of the head driving shaft 12 and is in a shape matching the cross-sectional shape of the head driving shaft 12 and in dimensions closely fitted with the cross-sectional dimensions of the head driving shaft 12, such that the driving bristle retainers 23-1, 23-2, 23-3, and 23-4 can be connected with the head driving shaft 12 without relative movement when the head driving shaft 12 is fitted into the holes. Preferably, the head driving shaft 12 has a circular cross section, and the holes on the driving bristle retainers 23-1, 23-2, 23-3, and 23-4 are round holes. Of course, the head driving shaft 12 and driving bristle retainers 23-1, 23-2, 23-3, and 23-4 can be formed integrally by injection molding, so as to obtain a connection without relative movement.

Please see FIGS. 10-14, similarly, the driven bristle retainers 21-1, 21-2, and 21-3 can be arranged in a top-to-bottom order in the $W_1$ direction of the axis $L_0$ of the holder driving shaft 14, for example, the third driven bristle retainer 21-3 can be arranged on the top, the second driven bristle retainer 21-2 can be arrange in the middle, and the first driven bristle retainer 21-1 can be arranged on the bottom. The bristles 27 can be fixed to the three driven bristle retainers 21-1, 21-2, and 21-3 respectively through any industrial brush manufacturing process. Each of the driven bristle retainers 21-1, 21-2, and 21-3 has a hole 210 that can be arranged around the axis $L_1$ of the head driving shaft 12 and is in a shape matching the cross-sectional shape of the head driving shaft 12 and in dimensions greater than the cross-sectional dimensions of the head driving shaft 12, to ensure that the head driving shaft 12 and the driven bristle retainers 21-1, 21-2, and 21-3 will not interfere with each other in the process of movement.

The driving bristle retainers 23-1, 23-2, 23-3, and 23-4 and the driven bristle retainers 21-1, 21-2, and 21-3 are arranged alternatively.

To enable the driving bristle retainers 23-1, 23-2, 23-3, and 23-4 to transfer the kinetic energy to the corresponding driven bristle retainers 21-1, 21-2, 21-3, for example, in this embodiment, each of the other driving bristle retainers 23-1, 23-2, and 23-3 except for the topmost fourth driving bristle retainer 23-4 has four protrusions, such as a first protrusion 233, a second protrusion 234, a third protrusion 235, and a fourth protrusion 236, wherein, the first protrusion 233 and the second protrusion 234 are arranged on the upper end face of the driving bristle retainer. These protrusions are arranged at intervals respectively on the end face in $W_1$ direction (i.e., upper end face) of each of the driving bristle retainers 23-1, 23-2, and 23-3 and the end face in $W_2$ direction (i.e., lower end face). As shown in FIG. 6, the first protrusion 233 and the second protrusion 234 are arranged on the upper end faces of the driving bristle retainer 23-1, 23-2, and 23-3 respectively. More precisely, the first protrusion 233 and the second protrusion 234 are arranged on the upper end face in a way that they are laterally symmetric in relation to the axis $L_1$ of the head driving shaft 12, i.e., the first protrusion 233 and the second protrusion 234 are configured at 180° to each other on the upper end face. Similarly, the third protrusion 235 and the fourth protrusion 236 are arranged on the lower end faces of the driving bristle retainers 23-1, 23-2, and 23-3 respectively. More precisely, the third protrusion 235 and the fourth protrusion 236 are arranged on the lower end face in a way that they are laterally symmetric in relation to the axis $L_1$ of the head driving shaft 12, i.e., the third protrusion 235 and the fourth protrusion 236 are configured at 180° to each other on the lower end face. The first protrusion 233 on the upper end face of each driving bristle retainer and the third protrusion 235 on the lower end face of the driving bristle retainer are arranged on the left of the axis $L_1$, and they are symmetric in relation to a plane that contains the center line of the driving bristle retainer in the thickness direction (i.e., $W_1$-$W_2$ direction) and is perpendicular to the axis $L_1$. The second protrusion 234 on the upper end face of each driving bristle retainer and the fourth protrusion 236 on the lower end face of the driving bristle retainer are arranged on the right of the axis $L_1$, and they are symmetric in relation to a plane that contains the center line of the driving bristle retainer in the thickness direction and is perpendicular to the axis $L_1$.

The protrusions 233, 234, 235, and 236 can be fitted as separate parts onto the corresponding end faces respectively, or, they can be formed integrally with the corresponding end faces by injection molding. In addition, there is no restriction on the quantity of the protrusions arranged on the driving bristle retainer; for example, the protrusions can be more than or less than four protrusions. Moreover, the protrusions arranged on different driving bristle retainers can be in the same quantity or in different quantities. For example, in this embodiment, four protrusions 233, 234, 235, and 236 are arranged on the driving bristle retainers 23-1, 23-2, and 23-3 respectively, while only two protrusions 235 and 236 are arranged on the driving bristle retainer 23-4. In addition, these protrusions can be in any shape, for example, they can have a facet or curved surface. Preferably, these protrusions have a partial cylindrical surface respectively.

FIGS. 6-9 show the relative positions of the protrusions 233, 234, 235, and 236 in detail. As shown in FIG. 7, in this embodiment, delimited by the axis $L_1$ of the head driving shaft 12 in $W_4$ direction, the left half of the driving bristle retainer is arranged with arc surfaces, wherein, the arc surface oriented to $W_1$ direction is denoted as 238, while the arc surface oriented to $W_2$ direction is denoted as 239. The arc surfaces 238 and 239 are shown more clearly in FIG. 8 and FIG. 9.

To enable the driven bristle retainers 21-1, 21-2, and 21-3 to receive the kinetic energy from the driving bristle retainers 23-1, 23-2, 23-3, and 23-4, in this embodiment, the driven bristle retainers 21-1, 21-2, and 21-3 are arranged with bevel faces at intervals on the end face in $W_1$ direction (i.e., the upper end face) and the end face in $W_2$ direction (i.e., the lower end face) respectively, for example, a first bevel face 213, a second bevel face 214, a third bevel face 215, and a fourth bevel face 216. These bevel faces correspond to the movement traces of the corresponding protrusions 233, 234, 235, and 236 on the driving bristle retainer respectively.

Figure 10:
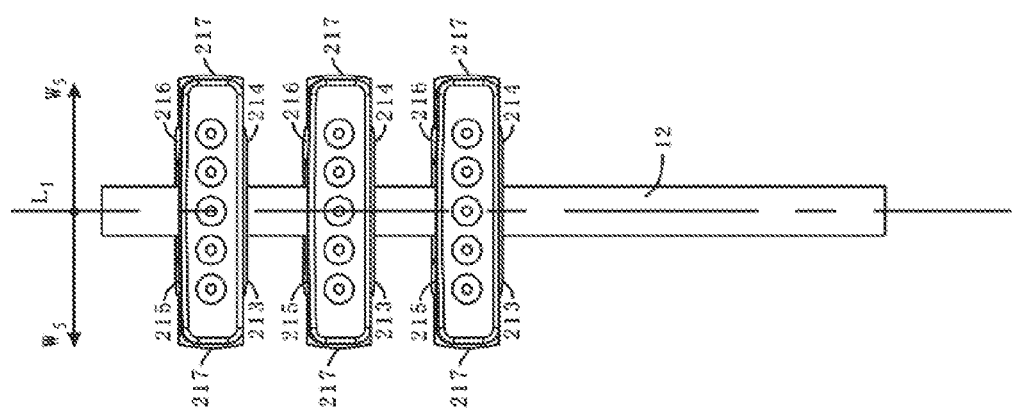
FIG. 10 is a front view, with the driving bristle retainers shown in FIG. 2 removed, showing a direction $W_5$ perpendicular to the axis of the head driving shaft, i.e., the length direction of the bristle retainers.

As shown in FIG. 10, the first bevel face 213 and the second bevel face 214 are arranged on the lower end faces of the driven bristle retainers 21-1, 21-2, and 21-3 respectively; more precisely, the first bevel face 213 is arranged on the left half of the lower end face delimited by the axis $L_1$ of the head driving shaft 12, while the second bevel face 214 is arranged on the right half of the lower end face delimited by the axis $L_1$ of the head driving shaft 12. The third bevel face 215 and the fourth bevel face 216 are arranged on the upper end faces of the driven bristle retainers 21-1, 21-2, and 21-3 respectively; more precisely, the third bevel face 215 is arranged on the left half of the upper end face delimited by the axis $L_1$ of the head driving shaft 12, while the fourth bevel face 214 is arranged on the right half of the upper end face delimited by the axis $L_1$ of the head driving shaft 12. The second bevel face 214 and the first bevel face 213 are in symmetric in relation to a plane defined by the axis $L_4$ and axis $L_1$, and the third bevel face 214 and the fourth bevel face 213 are in symmetric in relation to the plane defined by the axis $L_4$ and axis $L_1$.

Now, the arrangement of the first bevel face 213 will be described in the case of the driven bristle retainer 21-1. Obviously, the bevel face arrangements on other driven bristle retainers are similar to it. As shown in FIG. 13, with a plane that contains the vertexes of the head structure and is perpendicular to the axis $L_1$ of the head driving shaft 12 as a reference plane, the lower edge of the first bevel face 213 is defined as a lower start line 213A, while the upper edge of the first bevel face 213 is defined as an upper end line 213B. In this embodiment, the minimum distance from the upper end line 213B of the first bevel face 213 to the reference plane is greater than the minimum distance from the lower start line 213A of the first bevel face 213 to the reference plane, and the difference is denoted as $\Delta S_{213}$. That is to say, in $W_2$ direction, the line 213B is at $\Delta S_{213}$ from the line 213A. In operation, both the lower start line 213A and the upper end line 213B are in contact with the corresponding protrusions. When in contact, the lower start line 213A or the upper end line 213B forms a contact line of the bevel face with the corresponding protrusion. The lower start line 213A is closer to the driving bristle retainer than other contact lines of the bevel face with the corresonding protrusion, such that the driven bristle retainer is driven by the driving bristle retainer in the movement process. As shown in FIG. 13, a bevel extension part 213-1 is the upwardly extending part of the first bevel face 213, the edge at one end of the bevel extension part 213-1 is delimited by the line 213B, and the edge at the other end is delimited by a line projected from an axis $L_5$ at an revolving angle β from the axis $L_1$ of the head driving shaft 12 on the lower end face in $W_2$ direction. In this embodiment, the bevel extension part 213-1 is an area scanned by the upper end line 213B of the first bevel face 213 when the upper end line 213B revolves around the axis $L_1$ of the head driving shaft 12; therefore, the lines formed on the bevel extension part 213-1 by the upper end line 213B on the first bevel face 213 when the upper end line 213B scans are at the same minimum distance to the reference plane as the upper end line 213B on the first bevel face 213.

Likewise, as shown in FIG. 13, a bevel extension part 213-2 is the downwardly extending part of the first bevel face 213. The edge at one end of the bevel extension part 213-2 is delimited by the start line 213A on the first bevel face 213, and the edge at the other end is delimited by a line projected from the axis $L_5$ at an revolving angle β from the axis $L_1$ of the head driving shaft 12 on the end face in $W_2$ direction. In this embodiment, the bevel extension part 213-2 is an area scanned by the start line 213A of the first bevel face 213 when the start line 213A revolves around the axis $L_1$ of the head driving shaft 12; therefore, the lines formed on the bevel extension part 213-2 by the start line 213A on the first bevel face 213 when the start line 213A scans are at the same minimum distance to the reference plane as the start line 213A on the first bevel face 213. Furthermore, the lower end face has bevel extension parts 214-1, 214-2 of the second bevel face 214.

In this embodiment, the axis $L_1$ of the head driving shaft 12 is perpendicular to the movement axis $L_4$ of the first driven bristle retainer 21-1, and the second bevel face 214 and the first bevel face 213 are symmetric in relation to a plane defined by the axis $L_1$ of the head driving shaft 12 and the movement axis $L_4$ of the first driven bristle retainer 21-1. The bevel extension part 214-1 and the bevel extension part 213-1 are symmetric in relation to the plane defined by the axis $L_1$ of the head driving shaft 12 and the movement axis $L_4$ of the first driven bristle retainer 21-1. The bevel extension part 214-2 and the bevel extension part 213-2 are symmetric in relation to the plane defined by the axis $L_1$ of the head driving shaft 12 and the movement axis $L_4$ of the first driven bristle retainer 21-1.

Similarly, the upper end face has a third bevel face 215, a bevel extension part 215-1, a bevel extension part 215-2, a fourth bevel face 216, a bevel extension part 216-1, and a bevel extension part 216-2. As shown in FIG. 10, the third bevel face 215 and the first bevel face 213 are arranged on the upper end face and the lower end face respectively, and the fourth bevel face 216 and the second bevel face 214 are arranged on the upper end face and the lower end face respectively. The third bevel face 215 is arranged on the upper end face of the driven bristle retainer; more precisely, the third bevel face 215 is arranged on the left half of the upper end face delimited by the axis $L_1$ of the head driving shaft 12. In FIG. 14, it is shown that the third bevel face 215 is arranged on the right half of the upper end face delimited by the axis $L_5$ at a revolving angle β from the axis $L_1$ of the head driving shaft 12.

Now, the arrangement of the third bevel face 215 will be described in the case of the driven bristle retainer 21-1. Obviously, the bevel face arrangements on other driven bristle retainers are similar to it. As shown in FIG. 14, with a plane that contains the vertexes of the head structure and is perpendicular to the axis $L_1$ of the head driving shaft 12 as a reference plane, the lower edge of the third bevel face 215 is defined as a lower start line 215A, while the upper edge of the third bevel face 215 is defined as an upper end line 215B. In this embodiment, the minimum distance from the upper end line 215B of the third bevel face 215 to the reference plane is greater than the minimum distance from the lower start line 215A of the third bevel face 215 to the reference plane, and the difference is denoted as $\Delta S_{215}$. That is to say, in $W_2$ direction, the line 215B is at $\Delta S_{215}$ from the line 215A. As shown in FIG. 14, a bevel extension part 215-1 is the upwardly extending part of the third bevel face 215, the edge at one end of the bevel extension part 215-1 is delimited by the line 215B, and the edge at the other end is delimited by a line projected from an axis $L_5$ at an revolving angle β from the axis $L_1$ of the head driving shaft 12 on the upper end face in $W_1$ direction. In this embodiment, the bevel extension part 215-1 is an area scanned by the upper end line 215B of the third bevel face 215 when the upper end line 215B revolves around the axis $L_1$ of the head driving shaft 12; therefore, the lines formed on the bevel extension part 215-1 by the upper end line 215B on the third bevel face 215 when the upper end line 215B scans are at the same minimum distance to the reference plane as the upper end line 215B on the third bevel face 215.

Likewise, as shown in FIG. 14, a bevel extension part 215-2 is the downwardly extending part of the third bevel face 215. The edge at one end of the bevel extension part 215-2 is delimited by the start line 215A on the third bevel face 215, and the edge at the other end is delimited by a line projected from the axis $L_5$ at an revolving angle β from the axis $L_1$ of the head driving shaft 12 on the end face in $W_1$ direction. In this embodiment, the bevel extension part 215-2 is an area scanned by the start line 215A of the third bevel face 215 when the start line 215A revolves around the axis $L_1$ of the head driving shaft 12; therefore, the lines formed on the bevel extension part 215-2 by the start line 215A on the third bevel face 215 when the start line 215A scans are at the same minimum distance to the reference plane as the start line 215A on the third bevel face 215.

As shown in FIG. 14, each of the driven bristle retainers 21-1, 21-2, and 21-3 has a driven bristle retainer movement hole 219 on its bottom. The hole 219 is movably fitted with the corresponding driven bristle retainer movement shaft 329, and by the fitting of the holes 219 with the driven bristle retainer movement shafts 329, constrains the driven bristle retainers only to swing around the axes $L_2$, $L_3$, and $L_4$ of the driven bristle retainer movement shafts 329 respectively.

Please see FIGS. 13-17. Each of the driven bristle retainers 21-1, 21-2, and 21-3 has snap parts 211 that are arranged symmetrically; the outer side face of each snap part 211 is an arc surface 217, and the arc center of which is on the movement axis $L_2$, $L_3$, or $L_4$ of the corresponding driven bristle retainer 21-1, 21-2, or 21-3. The snap part 211 forms an upper flat surface 218 in $W_3$ direction, which is fitted with a slot surface 326 (FIG. 17) of the frame, and the upper flat surface 218 and the surface 326 always superpose each other partially in the movement process of the driven bristle retainer; therefore, the movement of the driven bristle retainer in $W_3$ direction is constrained by the fitting of the flat surface 218 with the surface 326, such that the driven bristle retainer is always constrained in the frame 32 in the entire movement process. The frame 32 has frame slots 325 (shown in FIG. 15), which are designed to accommodate the snap parts 211 of the corresponding driven bristle retainers. Each slot 325 on the frame 32 has an inner curved surface 327 corresponding to the arc surface 217 of the snap part; preferably, the inner curved surface 327 of the slot is an arc surface; preferably, the inner arc surface 327 of the slot shares the same center line with the corresponding arc surface 217 of the snap part when the arc surface 217 of the snap part is fitted with the inner arc surface 327 of the slot. In the movement process of a driven bristle retainer, the inner arc surface 327 of the slot and the arc surface 217 of the snap part always keep appropriate circumferential clearance, for example, the circumferential clearance can be with a range of 0.02 mm~0.08 mm.

In another embodiment, the driven bristle retainer movement holes 219 and the driven bristle retainer movement shafts 329 can be omitted. In such a case, the driven bristle retainers can be constrained to swing only around their respective movement axes $L_2$, $L_3$, and $L_4$, by means of the inner arc surfaces 327 of the slots and the arc surfaces 217 of the snap parts that are concentric with each other. In that case, preferably the circumferential clearance between the inner arc surface 327 of the slot and the arc surface 217 of the snap part is 0.02 mm~0.05 mm.

As shown in FIG. 15 and FIG. 16, the frame 32 has center blind holes 328 for movement of the driven bristle retainers, which are in the same quantity as the driven bristle retainers; the centers of the holes are on the corresponding movement axes $L_2$, $L_3$, and $L_4$ respectively. As shown in FIG. 16, the corresponding driven bristle retainer movement shaft 329, driven bristle retainer movement center hole 328, and driven bristle retainer movement hole 219 share the same axis. The driven bristle retainer movement center hole 328 is tightly fitted with the driven bristle retainer movement shaft 329, to ensure that the driven bristle retainer movement shaft 329 is connected with the driven bristle retainer movement center hole 328 without relative movement. Of course, they can be formed integrally by injection molding.

Figure 3:
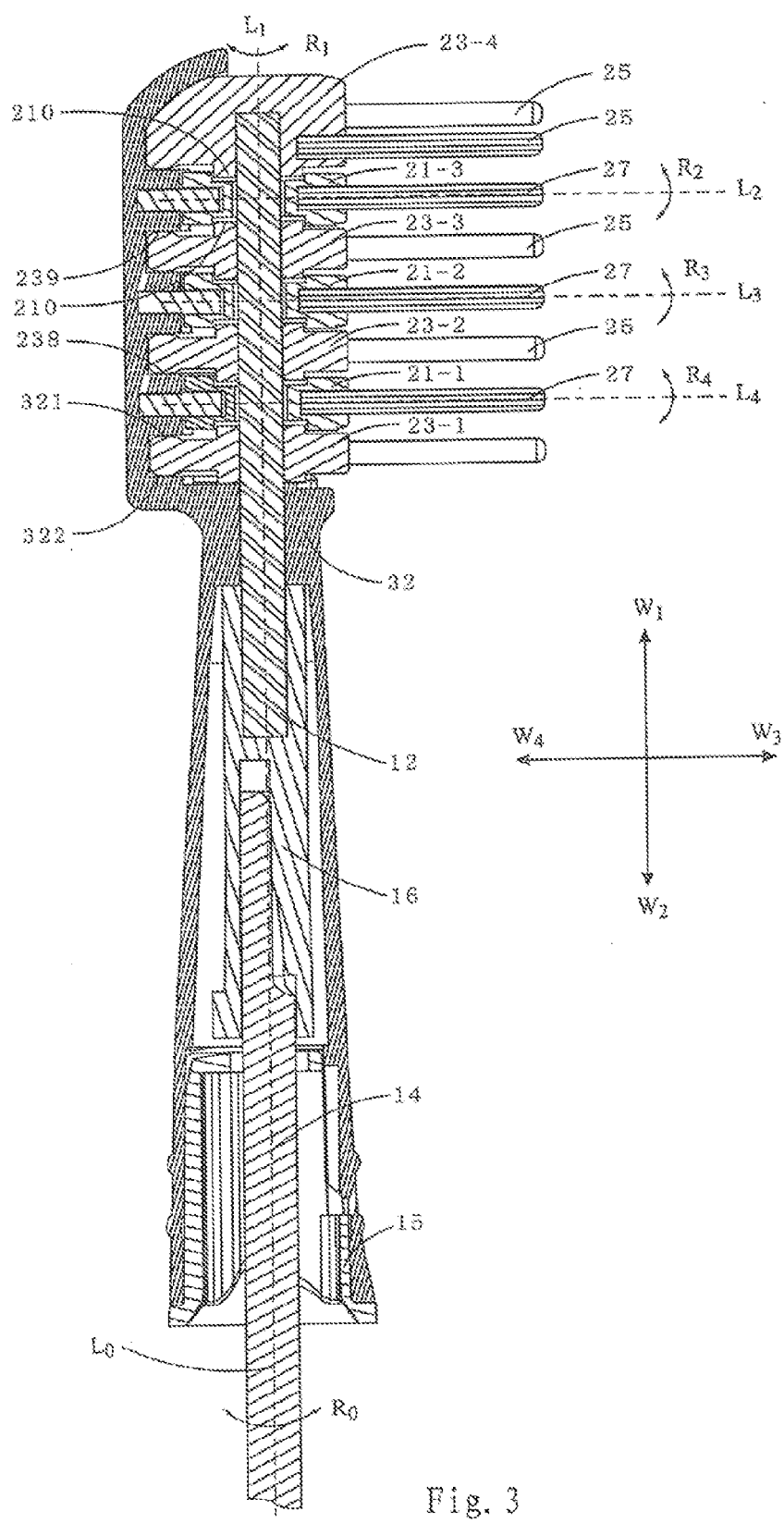
FIG. 3 is a sectional view of the brush part in FIG. 2 in direction A-A, showing a head driving shaft and bristle retainers, as well as upward direction $W_1$ and downward direction $W_2$ parallel to the axis of the head driving shaft, which also represent the thickness direction of the bristle retainers, and rightward direction $W_3$ and leftward direction $W_4$ perpendicular to the axis of the head driving shaft, which also represent the width direction of the bristle retainers.

As shown in FIG. 3, the frame 32 further comprises driving bristle retainer movement constraining planes that are in the same quantity as the driving bristle retainers. Among these driving bristle retainer movement constraining planes, the planes in $W_1$ direction are denoted, for example, as 322, and the planes in $W_2$ direction are denoted, for example, as 321. Each pair of constraining planes 322 and 321 that face each other accommodates a driving bristle retainer. The constraining plane 321 corresponds to the arc surfaces 239 on the edge of the lower part of the driving bristle retainer in $W_1$ direction, and the circumferential clearance between the constraining plane 321 and the arc surface 239 can be within a range of 0.03 mm~0.05 mm, for example. The constraining plane 322 corresponds to the arc surfaces 238 on the edge of the lower part of the driving bristle retainer in $W_2$ direction, and preferably the circumferential clearance between the constraining plane 322 and the arc surface 238 is 0.03 mm~0.05 mm. The constraining planes 321 and 322 can constrain any excessive movement of the driving bristle retainer in $W_1$ direction or $W_2$ direction.

As shown in FIG. 16, the frame 32 has a head driving shaft hole 3211, which share the same axis with the head driving shaft 12 and is in diameter slightly larger than the diameter of the head driving shaft 12, such that the head driving shaft 12 can move in relation to the head driving shaft hole 3211 with clearance. The head driving shaft 12 can be in any shape, preferably cylindrical shape, and in that case, the head driving shaft hole 3211 is a round hole. Preferably the diameter of the head driving shaft hole 3211 is larger than the diameter of the head driving shaft 12, for example, by 0.04 mm~0.09 mm.

Movement Analysis

As shown in the figures, when the first protrusion 233 on the driving bristle retainer 23-1 is fitted with the lower start line 213A of the first bevel face 213 of the driven bristle retainer 21-1, the second protrusion 234 on the driving bristle retainer 23-1 will be fitted with the upper end line 214B of the second bevel face 214 of the driven bristle retainer 21-1, the third protrusion 235 on the driving bristle retainer 23-2 will be fitted with the lower start line 215A of the third bevel face 215 of the driven bristle retainer 21-1, and the fourth protrusion 236 on the driving bristle retainer 23-2 will be fitted with the upper end line 216B of the fourth bevel face 216 of the driven bristle retainer 21-1.

When the first protrusion 233 on the driving bristle retainer 23-2 is fitted with the lower start line 213A of the first bevel face 213 of the driven bristle retainer 21-2, the second protrusion 234 on the driving bristle retainer 23-2 will be fitted with the upper end line 214B of the second bevel face 214 of the driven bristle retainer 21-2, the third protrusion 235 on the driving bristle retainer 23-3 will be fitted with the lower start line 215A of the third bevel face 215 of the driven bristle retainer 21-2, and the fourth protrusion 236 on the driving bristle retainer 23-3 will be fitted with the upper end line 216B of the fourth bevel face 216 of the driven bristle retainer 21-2.

When the first protrusion 233 on the driving bristle retainer 23-3 is fitted with the lower start line 213A of the first bevel face 213 of the driven bristle retainer 21-3, the second protrusion 234 on the driving bristle retainer 23-3 will be fitted with the upper end line 214B of the second bevel face 214 of the driven bristle retainer 21-3, the third protrusion 235 on the driving bristle retainer 23-4 will be fitted with the lower start line 215A of the third bevel face 215 of the driven bristle retainer 21-3, and the fourth protrusion 236 on the driving bristle retainer 23-4 will be fitted with the upper end line 216B of the fourth bevel face 216 of the driven bristle retainer 21-3.

Now, the analysis will be made in the case of the driven bristle retainer 21-1. When the driving bristle retainers 23-1, 23-2, 23-3, and 23-4 are driven by the head driving shaft 12 to move in clockwise direction (e.g., revolve by 60°) around the axis $L_1$, the first protrusion 233 on the driving bristle retainer 23-1 will move along the driven bristle retainer 21-1 in a direction from the lower start line 213A of the first bevel face 213 to the upper end line 213B of the first bevel face 213. Since there is a difference $\Delta S_{213}$ between the upper end line 213B and the lower start line 213A (i.e., the upper end line 213B is closer to the driving bristle retainer 23-1) and the movement of the driven bristle retainer 21-1 is constrained by the driven bristle retainer movement shaft 329 (i.e., the driven bristle retainer 21-1 can only swing around the axis $L_4$ of the driven bristle retainer movement shaft 329, the driven bristle retainer 21-1 can be driven the to move around the axis $L_4$ in clockwise direction under the synergistic action of the first protrusion 233 of the driving bristle retainer 23-1 and the first bevel face 213 of the driven bristle retainer 21-1, as the driving bristle retainer 23-1 swings.

When the first protrusion 233 on the driving bristle retainer 23-1 moves along the driven bristle retainer 21-1 from the lower start line 213A of the first bevel face 213 to the upper end line 213B, the driving bristle retainer 23-1 will revolve in clockwise direction around the axis $L_1$ by an angle γ, which may be 30°~70°, preferably 60°. Accordingly, the driven bristle retainer 21-1 will revolve in clockwise direction around the axis $L_4$ by an angle σ, which may be approximately 1°~8°, preferably 4°. The size of the angle σ depends on the size of $\Delta S_{213}$, which is to say, the greater the $\Delta S_{213}$ is, the greater the angle σ will be. The functional relationship (σ=f(γ)) between the angle σ and the angle γ can be set as required, and these changes are not beyond the scope of the present invention.

Likewise, when the fourth protrusion 236 on the driving bristle retainer 23-2 moves along the driven bristle retainer 21-1 from the upper end line 216B of the fourth bevel face 216 to the lower start line 216A, the fourth protrusion 236 on the driving bristle retainer 23-2 will attain the same effect as the first protrusion 233 on the driving bristle retainer 23-1, and the driving bristle retainer 23-2 will revolve in clockwise direction around axis $L_1$ by an angle γ. Accordingly, the driven bristle retainer 21-1 will revolve in clockwise direction around the axis $L_4$ by an angle σ. Similarly, the size of the angle σ depends on the size of $\Delta S_{216}$. In this embodiment, $\Delta S_{216} = \Delta S_{213}$; therefore, σ=4° when γ=60°.

It is seen from the analysis of the relationship between the second protrusion 234 on the driving bristle retainer 23-1 and the second bevel face 214 of the driven bristle retainer 21-1: the second protrusion 234 on the driving bristle retainer 23-1 moves along the second bevel face 214 of the driven bristle retainer 21-1 from the upper end line 214B to the lower start line 214A. Since there is a difference $\Delta S_{214}$ between the upper end line 214B and the lower start line 214A (i.e., the upper end line 214B is closer to the driving bristle retainer 23-1) and the second bevel face 214 and first bevel face 213 of the driven bristle retainer 21-1 are symmetric in relation to the plane defined by the axis $L_4$ and the axis $L_1$, the second bevel face 214 of the driven bristle retainer 21-1 permits the driven bristle retainer 21-1 to revolve around the movement axis $L_4$ by an angle $\sigma_1$, when the first protrusion 233 of the driving bristle retainer 23-1 moves in clockwise direction and drives the driven bristle retainer 21-1 to revolve around axis $L_4$ by the angle $\sigma_1$. That is to say, in the movement process, the second protrusion 234 doesn't interfere with the driven bristle retainer 21-1. i.e., the second bevel face 214 of the driven bristle retainer 21-1 will not hamper the movement of the driven bristle retainer 21-1. When the first protrusion 233 of the driving bristle retainer 23-1 stops at the upper end line 213B, the second protrusion 234 of the driving bristle retainer 23-1 will stop at the lower start line 214A.

Similarly, the relationship between the third protrusion 235 of the driving bristle retainer 23-2 and the third bevel face 215 of the driven bristle retainer 21-1 can be analyzed. The kinematic relation between the third protrusion 235 of the driving bristle retainer 23-2 and the third bevel face 215 of the driven bristle retainer 21-1 is the same as the kinematic relation between the second protrusion 234 of the driving bristle retainer 23-1 and the second bevel face 214 of the driven bristle retainer 21-1, and they attain the same effect.

It is seen from above analysis: when the first protrusion 233 of the driving bristle retainer is fitted with the lower start line 213A of the first bevel face 213 of the driven bristle retainer 21-1, the driving bristle retainer will begin to move around the axis $L_1$ in clockwise direction, and either or both of the first protrusion 233 on the driving bristle retainer 23-1 and the fourth protrusion 236 on the driving bristle retainer 23-2 will drive the driven bristle retainer 21-1 to move around the axis $L_4$ in clockwise direction; under the synergistic action of the second protrusion 234 of the driving bristle retainer 23-1 and the second bevel face 214 of the driven bristle retainer 21-1 and the synergistic action of the third protrusion 235 of the driving bristle retainer 23-2 and the third bevel face 215 of the driven bristle retainer 21-1, any interference with the movement of the driven bristle retainer 21-1 in clockwise direction can be effectively avoided.

Similarly, it is seen from above analysis: when the second protrusion 234 of the driving bristle retainer 23-1 is fitted with the lower start line 214A of the second bevel face 214 of the driven bristle retainer 21-1, the driving bristle retainer 23-1 will begin to move around the axis $L_1$ in counter-clockwise direction, and either or both of the second protrusion 234 on the driving bristle retainer 23-1 and the third protrusion 235 on the driving bristle retainer 23-2 will drive the driven bristle retainer 21-1 to move around the axis $L_4$ in counter-clockwise direction; under the synergistic action of the first protrusion 233 of the driving bristle retainer 23-1 and the first bevel face 213 of the driven bristle retainer 21-1 and the synergistic action of the fourth protrusion 236 of the driving bristle retainer 23-2 and the fourth bevel face 216 of the driven bristle retainer 21-1, any interference with the movement of the driven bristle retainer 21-1 can be effectively avoided.

The kinematic relation between any other driving bristle retainer and corresponding driven bristle retainer is the same as that described above, and for conciseness, will not be further detailed here.

Figure 4:
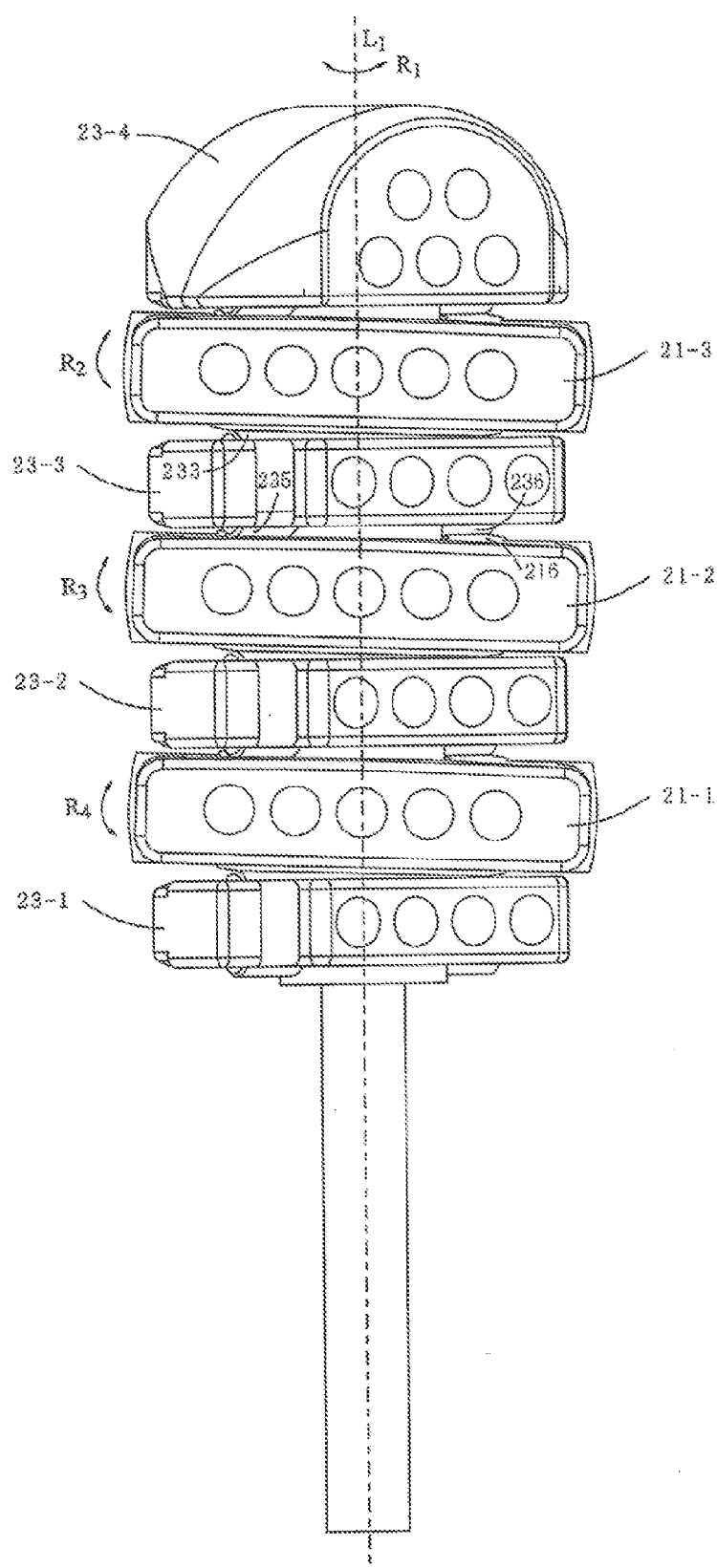
FIG. 4 illustrates the relative movement of the driving bristle retainer and driven bristle retainer.
Figure 8:
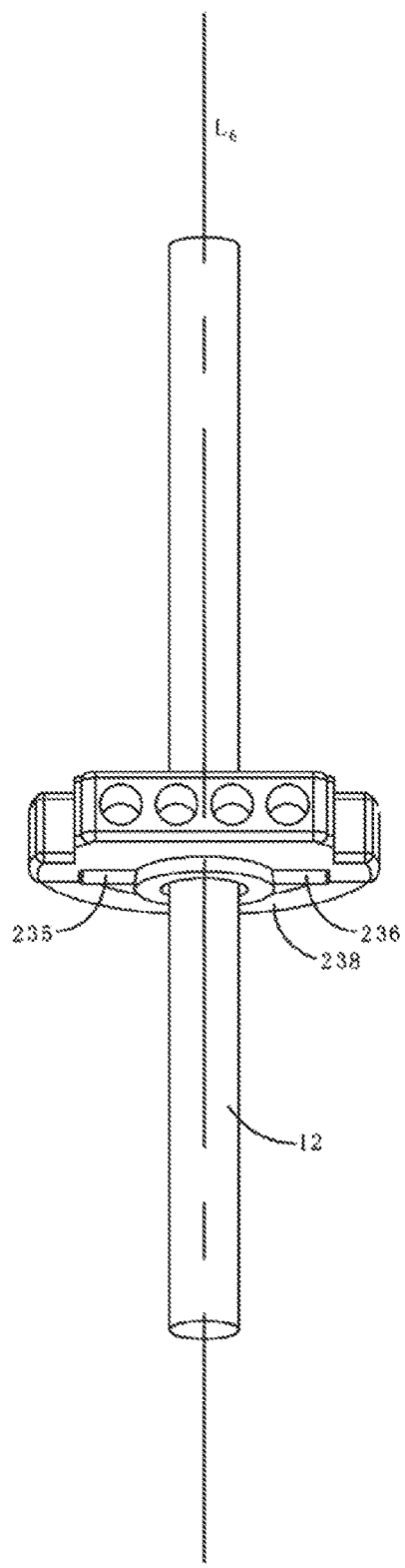
FIG. 8 is a perspective view illustrating the assembling relation between the driving bristle retainer and the head driving shaft.
Figure 9:
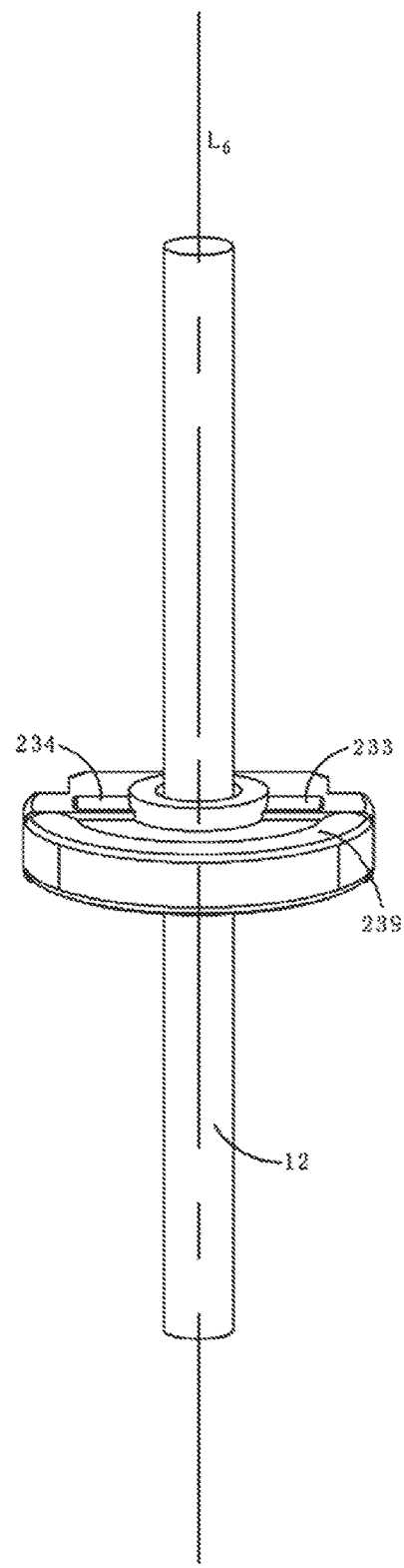
FIG. 9 is a rear view corresponding to FIG. 8.
Figure 12:
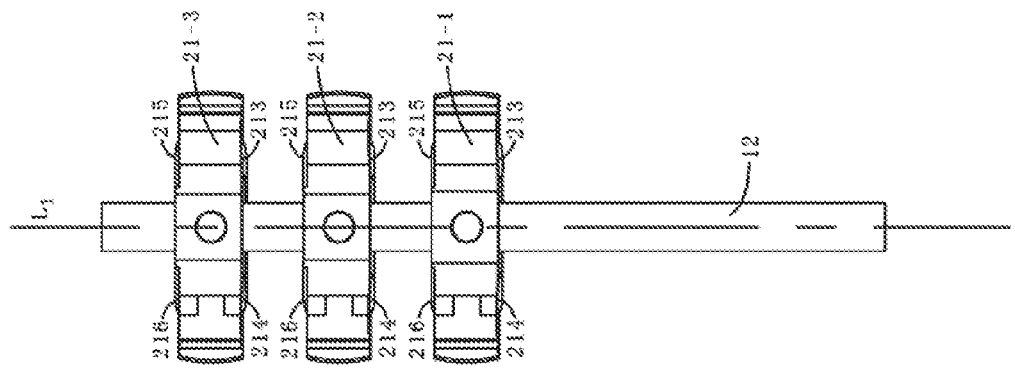
FIG. 12 is a rear view corresponding to FIG. 10.

When the first protrusion 233 of the driving bristle retainer is fitted with the upper end line 213B of the first bevel face 213 of the corresponding driven bristle retainer, the driving bristle retainers, driven bristle retainers, and head driving shaft 12 are in a motion state as shown in FIG. 4 and FIG. 5.

Likewise, when the driving bristle retainer moves around the axis $L_1$ in counter-clockwise direction, the second protrusion 234 and third protrusion 235 of the driving bristle retainer will drive the driven bristle retainer to move around the axis $L_4$ (or $L_2$ or $L_3$) in counter-clockwise direction; under the synergistic action of the first protrusion 233 of the driving bristle retainer and the first bevel face 213 of the driven bristle retainer and the synergistic action of the fourth protrusion 236 of the driving bristle retainer and the fourth bevel face 216 of the driven bristle retainer, any interference with the movement of the driven bristle retainer in counter-clockwise direction can be effectively avoided. Therefore, the third protrusion 235 of the driving bristle retainer attains the same effect as the second protrusion 234, and the fourth protrusion 236 attains the same effect as the first protrusion 233, whereas the effect of the third protrusion 235 or second protrusion 234 of the driving bristle retainer is opposite to the effect of the first protrusion 233 or fourth protrusion 236 of the driving bristle retainer during the operation.

In the present invention, with multiple groups of protrusions that are opposite in direction and a plurality of bevel faces that cooperate with the protrusions, the driven bristle retainers can move around their axes (e.g., $L_2$, $L_3$, or $L_4$) smoothly to and fro. Preferably, the movement axes (e.g., $L_2$, $L_3$, or $L_4$) of the driven bristle retainer are perpendicular to the axis $L_1$ of the head driving shaft, as shown in FIG. 3.

Furthermore, the movement axes of the driven bristle retainers can be arranged to be parallel to or superpose the axis $L_1$ of the head driving shaft or to be at any included angle from the axis $L_1$ of the head driving shaft.

Though the present invention is described above exemplarily in a case that the driving bristle retainers have protrusions arranged symmetrically and the driven bristle retainers have bevel faces arranged symmetrically, it should be appreciated that the protrusions on the driving bristle retainers and the bevel faces on the driven bristle retainers can be arranged in a non-symmetric pattern, as long as the protrusions and/or bevel faces don't hinder the movement of the driven bristle retainers when the driving bristle retainers drive the driven bristle retainers to move around their movement axes in clockwise or counter-clockwise direction under the synergistic action of the protrusions and the bevel faces.

As another embodiment, bevel faces can be arranged on the driving bristle retainers, while corresponding protrusions can be arranged on the driven bristle retainers. In such a case, the bevel faces are actuating parts, while the protrusions are driven parts; however, the kinematic relation between the bevel faces and the protrusions is similar to the kinematic relation described in the above embodiment, and for conciseness, will not be detailed further here.

Though the present invention is described in the embodiments exemplarily in a case of an electric toothbrush, the present invention is not limited to that; in other words, the present invention is also applicable to non-electric toothbrushes or other brushes.

It is obvious that the above description is exemplary, and various modifications and alternations falling into the scope of the attached claims may be made without departing from the spirit and scope of the present invention.

The invention claimed is:

1. A head structure of a brush appliance, comprising:
   a frame movably connected with a head driving shaft;
   a plurality of driving bristle retainers connected with the head driving shaft and driven by the head driving shaft, designed to receive bristles mounted on them; and
   one or more driven bristle retainers, which and the plurality of driving bristle retainers are alternatively arranged with each other, and designed to receive bristles mounted on them,
   wherein, the one or more driven bristle retainers are driven by the plurality of driving bristle retainers under a constraint of the frame to move around their respective movement axes;
   at least one of the plurality of driving bristle retainers has at least one protrusion on a surface perpendicular to an axis of the head driving shaft, and the one or more driven bristle retainers have at least one bevel face that cooperates with the at least one protrusion on their surfaces perpendicular to the axis of the head driving shaft where the one or more driven bristle retainers are driven by the plurality of driving bristle retainers; and
   at least one contact line on the at least one bevel face is closer to a driving bristle retainer than other contact lines of the bevel face with the corresponding protrusion, such that the driven bristle retainer is driven by the driving bristle retainer in the movement process.

2. The head structure as described in claim 1, wherein, the head driving shaft moves as a holder driving shaft of the brush appliance is driven by an electric motor to move.

3. The head structure as described in claim 1,
   wherein first and second protrusions that attain effects opposite to each other during an operation are arranged on the surface of the driving bristle retainer perpendicular to the axis of the head driving shaft, and bevel faces that cooperate with the respective protrusion are arranged on the corresponding surface of the driven bristle retainer driven by the driving bristle retainer;
   wherein the first protrusion is arranged on an upper surface of the driving bristle retainer along the axis of the head driving shaft, the second protrusion is arranged on a lower surface of the driving bristle retainer opposite to the upper surface, and both of the first protrusion and the second protrusion are on a same side in relation to the axis of the head driving shaft; and
   wherein when the first protrusion cooperates with the corresponding bevel face arranged on the corresponding driven bristle retainer to drive the driven bristle retainer to move, the second protrusion will cooperate with the corresponding bevel face arranged on the corresponding driven bristle retainer, without interference with a movement of the driven bristle retainer.

4. The head structure as described in claim 1,
   wherein first and second protrusions that attain effects opposite to each other during an operation are arranged on the surface of the driving bristle retainer perpendicular to the axis of the head driving shaft, and bevel faces that cooperate with the respective protrusion are arranged on the corresponding surface of the driven bristle retainer driven by the driving bristle retainer;

wherein both of the first protrusion and the second protrusion are arranged on an upper surface of the driving bristle retainer along the axis of the head driving shaft or both of them are arranged on a lower surface of the driving bristle retainer opposite to the upper surface, and the first protrusion and the second protrusion arranged on the upper surface or the lower surface are on different sides in relation to the axis of the head driving shaft; and wherein when the first protrusion and the corresponding bevel face arranged on the corresponding driven bristle retainer cooperate to drive the driven bristle retainer to move, the second protrusion and the corresponding bevel face arranged on the corresponding driven bristle retainer cooperate, without interference with a movement of the driven bristle retainer.

5. The head structure as described in claim 1,
wherein each of the plurality of driving bristle retainers has first and second groups of protrusions;
wherein the first group of protrusions is opposite in protruding direction to the second group of protrusions;
wherein the first group of protrusions is arranged on an upper surface of the driving bristle retainer along the axis of the head driving shaft, in bilateral symmetry in relation to the axis of the head driving shaft, while the second group of protrusions is arranged on a lower surface of the driving bristle retainer opposite to the upper surface, in bilateral symmetry in relation to the axis of the head driving shaft; and
wherein in the first group and second group of protrusions, the protrusions that are opposite in protruding direction to each other and on a same side in relation to the axis of the head driving shaft are symmetric in relation to a plane that contains a center line of the corresponding driving bristle retainer in a thickness direction and is perpendicular to the axis of the head driving shaft.

6. The head structure as described in claim 1, wherein the movement axes of the one or more driven bristle retainers are perpendicular to the axis of the head driving shaft.

7. The head structure as described in claim 1, wherein the plurality of driving bristle retainers swing around the axis of the head driving shaft, and the one or more driven bristle retainers swing around their respective movement axes.

8. The head structure as described in claim 7, wherein the plurality of driving bristle retainers revolve around the axis of the head driving shaft by an angle γ, and accordingly the one or more driven bristle retainers revolve around their respective movement axes by an angle σ.

9. The head structure as described in claim 8, wherein the angle γ is 30°~70°, and the angle σ is 1°~8°.

10. The head structure as described in claim 9, wherein the angle γ is 60°, and the angle σ is 4°.

11. A head structure of a brush appliance, comprising:
a frame movably connected with a head driving shaft;
a plurality of driving bristle retainers connected with the head driving shaft and driven by the head driving shaft, designed to receive bristles mounted on them; and
one or more driven bristle retainers, which and the plurality of driving bristle retainers are alternatively arranged with each other, and designed to receive bristles mounted on them,
wherein, the one or more driven bristle retainers are driven by the plurality of driving bristle retainers under a constraint of the frame to move around their respective movement axes;
at least one of the plurality of driving bristle retainers has at least one bevel face on a surface perpendicular to an axis of the head driving shaft, and the one or more driven bristle retainers have at least one protrusion that cooperates with the at least one bevel face on their surfaces where the one or more driven bristle retainers are driven by a driving bristle retainer; and
at least one driven line on the at least one bevel face is closer to the driven bristle retainer than other contact lines of the at least one bevel face with the corresponding protrusion, such that the one or more driven bristle retainers are driven by the plurality of driving bristle retainers in the movement process.

12. The head structure as described in claim 11, wherein, the head driving shaft moves as a holder driving shaft of the brush appliance is driven by an electric motor to move.

13. The head structure as described in claim 11,
wherein first and second bevel faces that attain effects opposite to each other during an operation are arranged on the surface of the driving bristle retainer perpendicular to the axis of the head driving shaft, and protrusions that cooperate with the first and second bevel faces are arranged on the corresponding surface of the driven bristle retainer driven by the driving bristle retainer;
wherein the first bevel face is arranged on an upper surface of the driving bristle retainer along the axis of the head driving shaft, the second bevel face is arranged on a lower surface of the driving bristle retainer opposite to the upper surface, and both of the first bevel face and the second bevel face are on a same side in relation to the axis of the head driving shaft; and
wherein when the first bevel face cooperates with the corresponding protrusion arranged on the corresponding driven bristle retainer to drive the driven bristle retainer to move, the second bevel face will cooperate with the corresponding protrusion arranged on the corresponding driven bristle retainer, without interference with a movement of the driven bristle retainer.

14. The head structure as described in claim 11,
wherein first and second bevel faces that attain effects opposite to each other during an operation are arranged on the surface of the driving bristle retainer perpendicular to the axis of the head driving shaft, and protrusions that cooperate with the first and second bevel faces are arranged on the corresponding surface of the driven bristle retainer driven by the driving bristle retainer;
wherein both of the first bevel face and the second bevel face are arranged on an upper surface of the driving bristle retainer along the axis of the head driving shaft or both of them are arranged on a lower surface of the driving bristle retainer opposite to the upper surface, and the first bevel face and the second bevel face arranged on the upper surface or the lower surface are on different sides in relation to the axis of the head driving shaft; and
wherein when the first bevel face cooperates with the corresponding protrusion arranged on the corresponding driven bristle retainer to drive the driven bristle retainer to move, the second bevel face will cooperate with the corresponding protrusion arranged on the corresponding driven bristle retainer, without interference with a movement of the driven bristle retainer.

15. The head structure as described in claim 11,
wherein the driving bristle retainer has first and second groups of bevel faces;

wherein the first group of bevel faces is arranged on a lower surface of the driving bristle retainer along the axis of the head driving shaft, in bilateral symmetry in relation to the axis of the head driving shaft, while the second group of bevel faces is arranged on an upper surface of the driving bristle retainer opposite to the lower surface, in bilateral symmetry in relation to the axis of the head driving shaft; and wherein the first group of bevel faces is symmetric in relation to a plane that contains a center line of the corresponding driving bristle retainer in a thickness direction and is perpendicular to the axis of the head driving shaft, and the second group of bevel faces is formed by revolving the first group of bevel faces by 180° around the axis of the head driving shaft.

16. The head structure as described in claim 11, wherein the movement axes of the one or more driven bristle retainers are perpendicular to the axis of the head driving shaft.

17. The head structure as described in claim 11, wherein the plurality of driving bristle retainers swing around the axis of the head driving shaft, and the one or more driven bristle retainers swing around their respective movement axes.

18. The head structure as described in claim 17, wherein the plurality of driving bristle retainers revolve around the axis of the head driving shaft by an angle $\gamma$, and accordingly the one or more driven bristle retainers revolve around their respective movement axes by an angle $\sigma$.

19. The head structure as described in claim 18, wherein the angle $\gamma$ is 30°~70°, and the angle $\sigma$ is 1°~8°.

20. The head structure as described in claim 19, wherein the angle $\gamma$ is 60°, and the angle $\sigma$ is 4°.

* * * * *